United States Patent [19]

Shields

[11] Patent Number: 5,207,704
[45] Date of Patent: May 4, 1993

[54] POSTURE BOARD

[76] Inventor: Mary Shields, 9 East Drive, Toronto, Ontario, M6N 2N8, Canada

[21] Appl. No.: 790,527

[22] Filed: Nov. 12, 1991

[51] Int. Cl.$^5$ .............................................. A61F 5/00
[52] U.S. Cl. .................................. 606/240; 128/845; 5/652
[58] Field of Search ...................... 606/237, 240, 241; 602/6, 19, 32, 35; 128/845, 846, 870, 376, 377, 68, 69; 297/284 C-284 E; 5/652-654, 630, 644, 636; 482/140, 142; 280/16-19

[56] References Cited

U.S. PATENT DOCUMENTS

| | | | |
|---|---|---|---|
| 1,833,426 | 11/1931 | Knudson | 606/240 |
| 1,904,039 | 4/1933 | Bruder | 606/240 |
| 2,558,105 | 6/1951 | Schinman | 606/240 X |
| 2,937,032 | 5/1960 | McKelvey | 280/18 X |
| 3,199,887 | 8/1965 | McKelvey | 280/18 |
| 3,348,880 | 10/1967 | Swann | 297/284 D X |
| 3,359,577 | 12/1967 | Rogers | 5/652 X |
| 3,446,531 | 5/1969 | Froelich | 297/284 D |
| 3,680,548 | 8/1972 | Brown | 606/237 |
| 3,794,341 | 2/1974 | Torok | 280/18 |
| 3,877,750 | 4/1975 | Scholpp | 5/652 X |
| 4,024,861 | 5/1977 | Vincent | 128/870 X |
| 4,230,099 | 10/1980 | Richardson | 606/240 |
| 4,300,249 | 11/1981 | Taylor | 128/377 X |
| 4,350,152 | 9/1982 | Strakowski | 5/630 X |
| 4,350,388 | 9/1982 | Weiner | 297/284 D X |
| 4,431,232 | 2/1984 | Hannouche | 297/284 D X |
| 4,678,445 | 7/1987 | Monreal | 280/18 X |
| 4,718,724 | 1/1988 | Quinton et al. | 297/284 D |
| 4,752,067 | 6/1988 | Colonello | 482/140 |
| 4,796,315 | 1/1989 | Crew | 606/240 X |
| 4,903,412 | 2/1990 | Pedrow | 606/240 X |
| 4,993,164 | 2/1991 | Jacobsen | 297/284 C X |
| 5,033,137 | 7/1991 | Pedrow | 5/636 |
| 5,070,865 | 12/1991 | Iams | 606/240 |
| 5,076,643 | 12/1991 | Colasanti et al. | 297/284 E |

FOREIGN PATENT DOCUMENTS 9011741 10/1990 World Int. Prop. O. .

Primary Examiner—Richard J. Apley
Assistant Examiner—Linda C. M. Dvorak

[57] ABSTRACT

The posture board according to the present invention is contoured to a spinal mating shape. The board comprises an upper back supporting portion having a leading edge and a lower back supporting portion terminating in a trailing edge. The board has a longitudinally extending sine wave configuration with an up curve at the lower back supporting portion. The board further has a side to side concave curvature defining a trough like center region and upwardly turned outside edges. The center region along at least part of the upper back supporting portion and at the trailing edge is in contact with the supporting surface on which the posture board is used. The up curve defines a gap beneath the center region along the lower back supporting portion and the supporting surface. The outside edges of the board are more flexible than the center region to allow some edge flattening while the center region is much less flexible to prevent lengthwise full flattening of the board at the center region under weight of a user such that the board provides vibratory feedback responsive to body vibrations given off by the user.

2 Claims, 3 Drawing Sheets

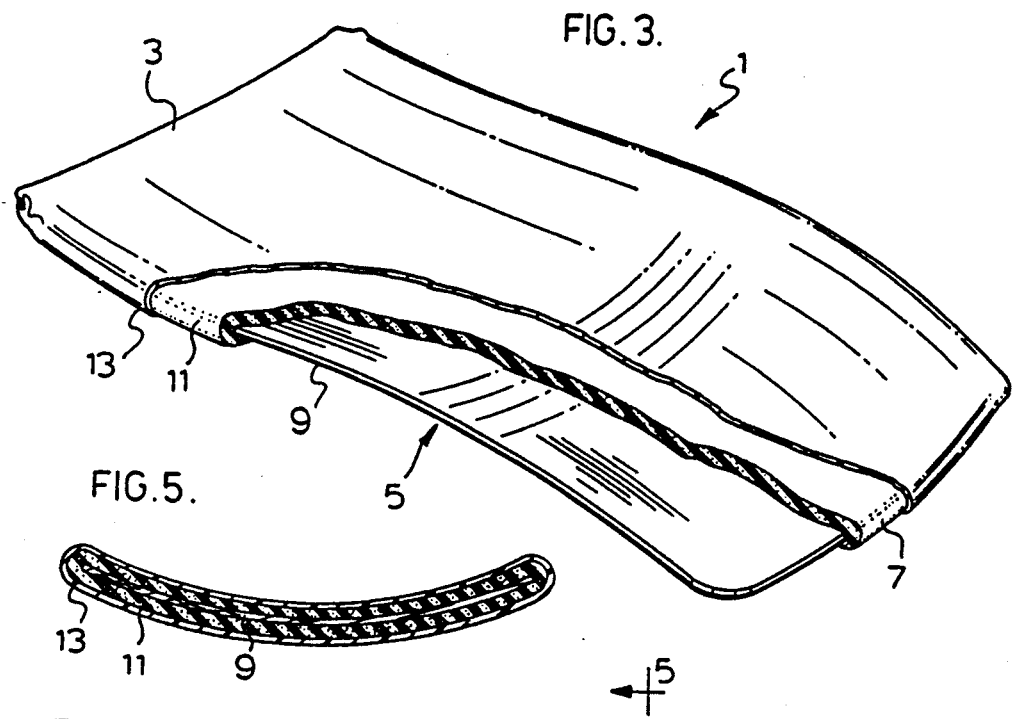
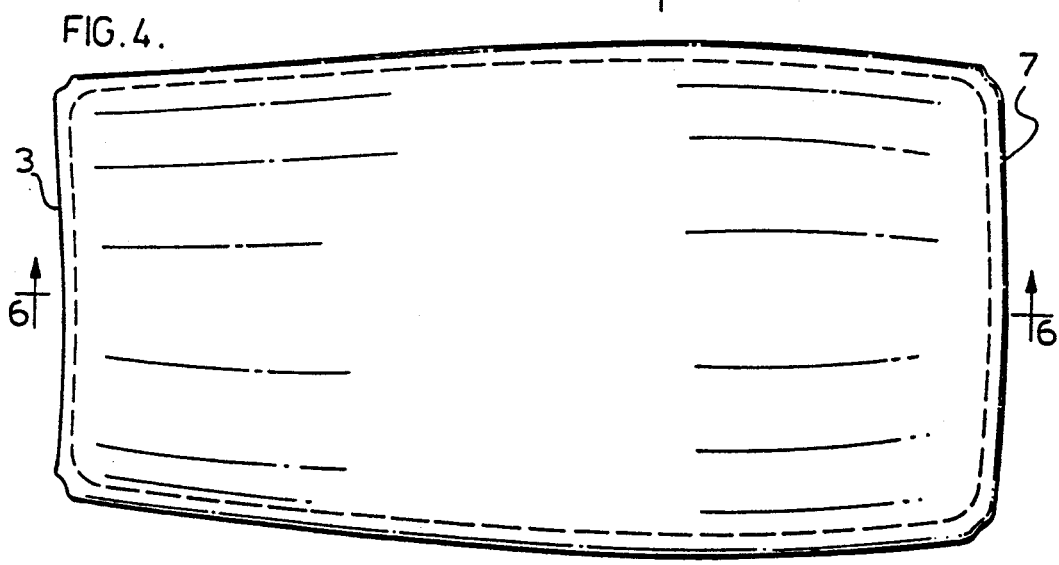
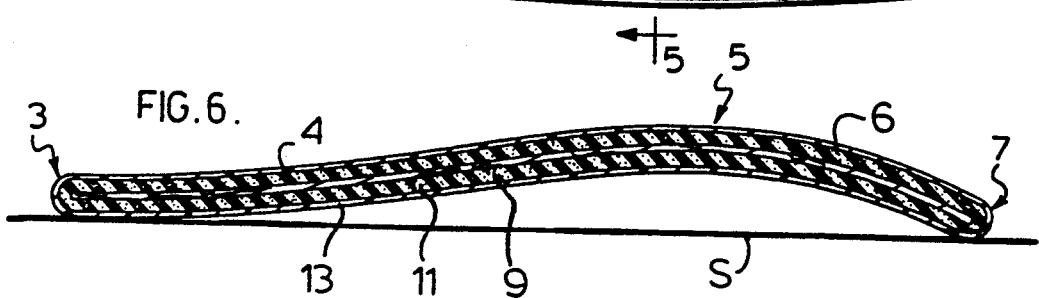

POSTURE BOARD

FIELD OF THE INVENTION

The present invention relates to a posture board or back support.

BACKGROUND OF THE INVENTION

Many people suffer from back problems. One of the primary causes for back problems is incorrect posture when sitting, standing and lying down.

There are presently available a relatively limited number of effective back supporting aids. Those that are available are usually nothing more than thick pads for cushioning the back. These types of thick pads do not provide adequate posture training nor are they sensitive to natural vibrations given off by the body.

SUMMARY OF THE PRESENT INVENTION

The present invention provides a posture board or back support usable in either a sitting or a lying mode and specifically designed to not only mate with the contour of the back or spinal region but to also cooperate with natural body rhythms particularly inducive to training the spinal region to assume a position of correct posture. In particular the posture board of the present invention is contoured to a spinal mating shape and comprises an upper back supporting portion having a leading edge and a lower back supporting portion terminating in a trailing edge. The board has a longitudinally extending sine wave configuration with an up curve at the lower back supporting portion. The board also has a side to side concave curvature defining a trough like center region with upwardly turned outside edges. The center region along at least part of the upper back supporting portion and at the trailing edge of the board is in contact with the supporting surface on which the posture board is used. The up curve defines a gap between the center region along the lower back supporting portion and the supporting surface. The board is more flexible and bends downwardly at its outside edges while being less flexible at the center region to prevent full lengthwise flattening of the board under weight of a user thereby providing vibratory feedback responsive to body vibrations given off by the user.

BRIEF DESCRIPTION OF THE DRAWINGS

The above as well as other advantages and features of the present invention will be described in greater detail according to the preferred embodiments of the present invention in which;

FIG. 3 is a further perspective view showing in cut away the posture board of FIG. 2;

FIG. 4 is a top plan view of the posture board of FIG. 2;

FIG. 5 is a sectional view along the lines 5—5 of FIG. 4;

FIG. 6 is a sectional view along the lines 6—6 of FIG. 4;

Figure 1:
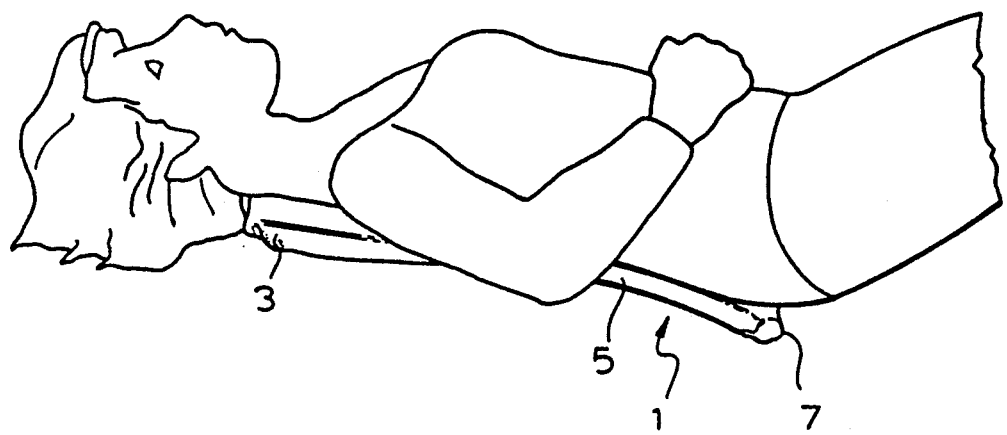
FIG. 1 shows a person in a supine position using a posture board in accordance with a preferred embodiment of the present invention.
Figure 2:
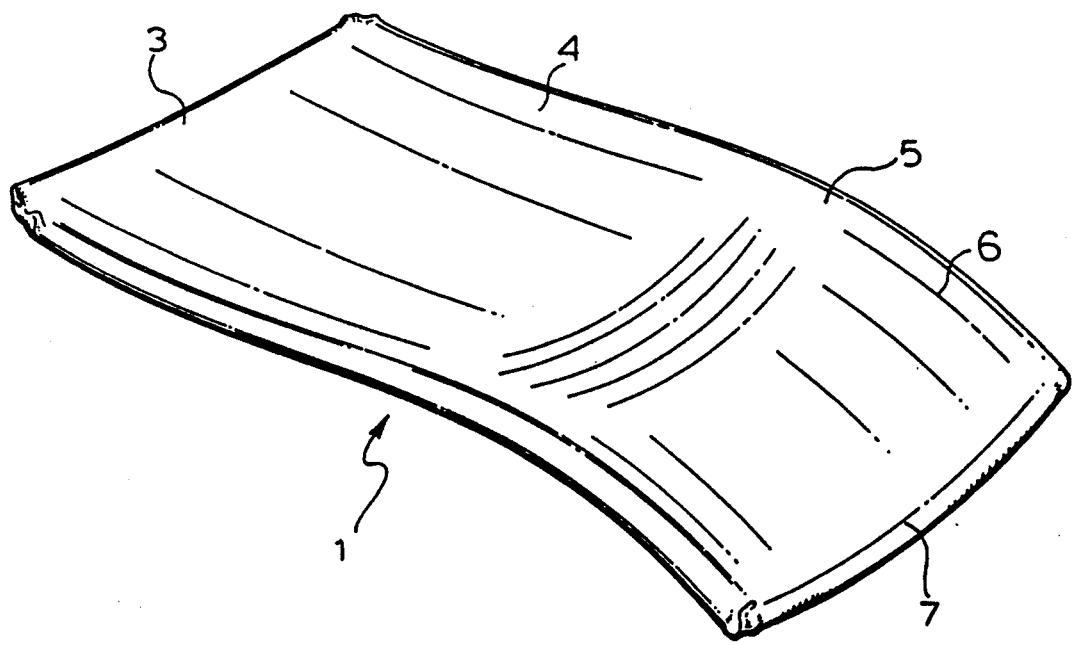
FIG. 2 is a perspective view of the posture board used by the person of FIG. 1.

Detailed Description According to the Preferred Embodiments of the Present Invention in Which:

FIG. 1 shows an individual lying down on a posture board or back support generally indicated at 1. The posture board has sine wave like configuration beginning with a leading edge 3 of upper back supporting portion 4 extending down to a high point or pinnacle region 5 continuing to a lower back supporting portion 6 which terminates in a trailing edge 7. The pinnacle region is about two-thirds along the length of the posture board so that the upper back supporting portion 4 is of increased length relative to the lower back supporting portion 6. In the preferred embodiment, the posture board has an overall length of about one and a half feet with the pinnacle region 5 being located about a foot from the leading edge of the board.

In the embodiment shown, the board has a layered construction. This layered construction is based on an interior core layer 9 which is made of wood. The wood is covered with a padded foam layer 11 covered outwardly by a protective cover or skin 13. The foam layer is preferably no more than about one quarter of an inch in thickness and cover 13 is preferably made from a vinyl or vinyl-like material which is easily cleanable and which is relatively low in cost for manufacturing of the board.

In another embodiment the posture board is constructed from a single piece of plastic or other similar material having the same spinal mating configuration as described above. With this shape and as a result of the board's flex characteristics, to be described later in detail, the board is able to pick up the vibrational characteristics naturally given off by body rhythms of the user. These body rhythms are classified as primary rhythms resulting from the flow of spinal fluid through the body and respiratory rhythms which occur as the result of breathing. The shape and flex of the board provide it with vibrational characteristics such that it is able to tune itself with the body rhythms and provide a vibratory feedback which matches that of the body.

Figure 7:
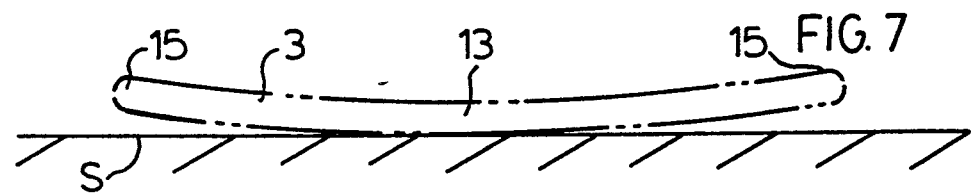
FIG. 7 is an end view showing the leading edge of the posture board of FIG. 2.
Figure 9:
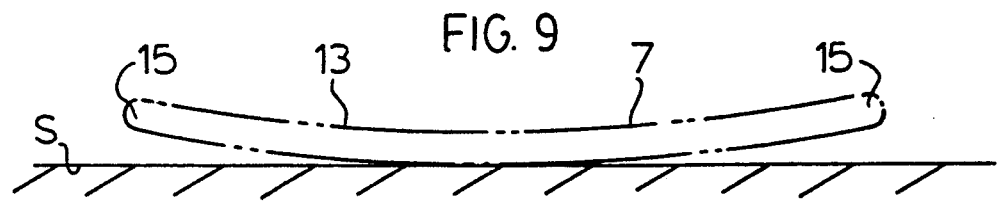
FIG. 9 is an end view of the trailing edge of the posture board of FIG. 2.

FIGS. 7 and 9 show that the board has a side to side concave curvature with upwardly curved outside edges 15 and a depressed or trough like center region 13. Without the weight of the user on the board, it is in contact with a supporting surface S at both its leading and its trailing edges along the center region. As best seen in FIG. 6 of the drawings, the center region also contacts the supporting surface part way along the upper back supporting portion and is gapped from the supporting surface at the pinnacle of the lower back supporting portion.

Figure 8:
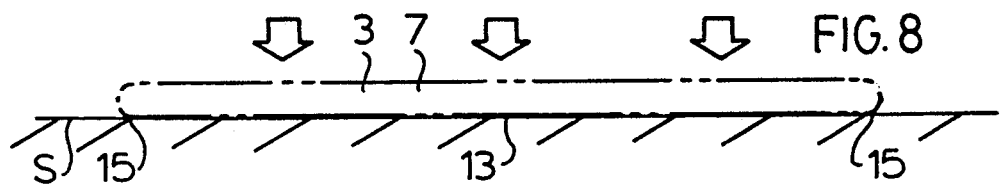
FIG. 8 shows downward flexing of the leading edge shown in FIG. 7.
Figure 10:
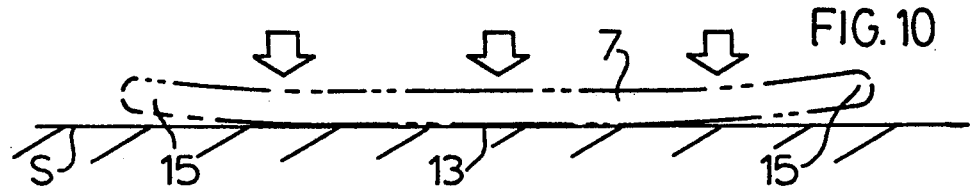
FIG. 10 shows downward flexing of the trailing edge shown in FIG. 9.

The board has a flex pattern which varies from one part of the board to another. In particular, as can be seen in FIG. 8 of the drawings, the board is relatively flexible at its outside edges particularly at its leading edge 3 such that the board will essentially flatten under the weight of a user from side to side at the leading edge. The outside edge of the board at the trailing edge as represented in FIGS. 9 and 10 have a greater up curvature than at the leading edge and are slightly stiffer so that although they do flex downwardly, they do not flatten to the extent of that found at the leading edge of the board under the weight of the user.

The center region of the board is relatively stiff or inflexible compared to the outside edges and is sufficiently strong that it will not allow lengthwise flattening of the board under weight of a user, even a person of very substantial size, thereby maintaining the gap between it and the supporting surface at the lower back supporting portion of the board. As a result, much of the board remains elevated from ground level. However, the center region at the gap is not without some flex and is therefore able to respond to the body rhythms given off by the user as earlier described, i.e. because the board does not completely flatten lengthwise onto the supporting surface, it is able to move up and down with the body rhythms.

The side to side curvature of the board provides a proper fit and feel for the user to center himself or herself on the board. As the board flattens from side to side under weight, particularly at its leading edge near the shoulders of the user as best seen in FIG. 1, it provides a much wider support or base beneath the user which substantially eliminates any side to side rocking of the board while in use.

Although various preferred embodiments of the invention have been described in detail, it will be appreciated by those skilled in the art that variations may be made without departing from the spirit of the invention or the scope of the appended claims.

The embodiments of the invention in which an exclusive property or privilege is claimed are defined as follows:

1. A posture board contoured to a spinal mating shape comprising an upper back supporting portion having a leading edge and a lower back supporting portion terminating in a trailing edge, said board having a longitudinally extending sine wave configuration with an up curve at said lower back supporting portion and a side to side concave curvature defining a center region with upwardly turned outside edges, said enter region, along at least part of said upper back supporting portion and at said trailing edge being in contact with a supporting surface on which said posture board is used, said up curve defining a gap between said center region along said lower back supporting portion and such supporting surface, said outside edges being relatively flexible to allow downward bending of said edges, said center region being less flexible than said edges and preventing lengthwise flattening of said board under weight of a user such that said board provides vibratory feedback responsive to body vibrations given off by the user, said posture board having a lesser side to side concave curvature at said leading edge than at said trailing edge of said board.

2. A posture board as claimed in claim 1, wherein said outside edges at said leading edge are more flexible than said outside edges at said trailing edge.

* * * * *